US012678382B2

(12) United States Patent
    Yoshida

(10) Patent No.: US 12,678,382 B2
(45) Date of Patent: Jul. 14, 2026

(54) WATER-IN-OIL TYPE EMULSIFIED SOLID COSMETIC MATERIAL

(71) Applicant: SHISEIDO COMPANY, LTD., Tokyo (JP)

(72) Inventor: Rina Yoshida, Tokyo (JP)

(73) Assignee: SHISEIDO COMPANY, LTD., Tokyo (JP)

(*) Notice: Subject to any disclaimer, the term of this patent is extended or adjusted under 35 U.S.C. 154(b) by 208 days.

(21) Appl. No.: 18/563,721

(22) PCT Filed: Jun. 16, 2022

(86) PCT No.: PCT/JP2022/024095
    § 371 (c)(1),
    (2) Date: Nov. 22, 2023

(87) PCT Pub. No.: WO2022/270398
    PCT Pub. Date: Dec. 29, 2022

(65) Prior Publication Data
    US 2024/0238174 A1    Jul. 18, 2024

(30) Foreign Application Priority Data
    Jun. 22, 2021    (JP) ................................. 2021-103338

(51) Int. Cl.
    *A61K 8/06*        (2006.01)
    *A61Q 1/02*        (2006.01)
    *A61Q 17/04*       (2006.01)

(52) U.S. Cl.
    CPC .............. *A61K 8/064* (2013.01); *A61Q 1/02* (2013.01); *A61Q 17/04* (2013.01); *A61K 2800/592* (2013.01)

(58) Field of Classification Search
    None
    See application file for complete search history.

(56) References Cited

U.S. PATENT DOCUMENTS

2004/0258721 A1    12/2004    Bauer et al.

FOREIGN PATENT DOCUMENTS

| | | |
|---|---|---|
| JP | 2002-097111 A | 4/2002 |
| JP | 2005-508919 A | 4/2005 |
| JP | 2013-053072 A | 3/2013 |
| KR | 2009-0121848 A | 11/2009 |
| WO | WO-2006/028308 A1 | 3/2006 |

OTHER PUBLICATIONS

International Searching Authority, "International Search Report," issued in connection with International Patent Application No. PCT/JP2022/024095, dated Aug. 2, 2022.
International Searching Authority, "Written Opinion," issued in connection with International Patent Application No. PCT/JP2022/024095, dated Aug. 2, 2022.
PCT International Preliminary Report on Patentability, dated Jan. 4, 2024, which includes a Translation of International Searching Authority, "Written Opinion," issued in connection with International Patent Application No. PCT/JP2022/024095, dated Aug. 2, 2022.

*Primary Examiner* — Nannette Holloman
(74) *Attorney, Agent, or Firm* — Foley & Lardner LLP

(57)    ABSTRACT

The present invention provides a water-in-oil type emulsified solid cosmetic material excellent in stability and usability.
The water-in-oil type emulsified solid cosmetic material according to the present invention comprises an oily component (A), an aqueous component (B), and a powder component (C). Then, the oily component comprises a polar oil component and a wax component, the wax component comprises an ester wax, a ratio of a total mass of the polar oil component to a total mass of the ester wax is 20 to 70, and a content of the polar oil component with respect to a total mass of the water-in-oil type emulsified solid cosmetic material is 9 to 30 mass %.

8 Claims, No Drawings

WATER-IN-OIL TYPE EMULSIFIED SOLID COSMETIC MATERIAL

CROSS-REFERENCE TO RELATED APPLICATIONS

The present application claims priority under 35 U.S.C. § 371 to International Patent Application No. PCT/JP2022/024095, filed Jun. 16, 2022, which claims priority to and the benefit of Japanese Patent Application No. 2021-103338, filed Jun. 22, 2021. The contents of these applications are hereby incorporated by reference in their entireties.

TECHNICAL FIELD

The present invention relates to a water-in-oil type emulsified solid cosmetic material.

BACKGROUND ART

Cosmetic materials take various dosage forms depending on applications, and an emulsified solid cosmetic material may be used for make-up cosmetics, sunscreen cosmetics, and the like. Examples of the emulsified solid cosmetic material include a water-in-oil type emulsified solid cosmetic material obtained by solidifying an external oil phase with an oily solidifying agent, and an oil-in-water type emulsified solid cosmetic material obtained by solidifying an external water phase with an aqueous solidifying agent.

Among these, water-in-oil type emulsified solid cosmetic materials generally have high water resistance, and thus are suitable for sunscreen cosmetic materials and the like that are used in an environment where water wetting or the like easily occurs. However, for example, when the content of an oily component such as polar oil is increased in order to maintain a high sunscreening effect, discomfort tends to occur when a cosmetic is applied to the skin. In order to ameliorate such discomfort, it has also been studied to increase a moisture content of a solid emulsifier. However, when the moisture content is increased with respect to the water-in-oil type emulsified solid cosmetic material having a high oily component content, so-called sweating in which water droplets float on a surface of a cosmetic material may occur.

CITATION LIST

Patent Literature

Patent Literature 1: JP 2002-097111 A

SUMMARY OF THE INVENTION

Object of the Invention

As described above, in the conventional water-in-oil type emulsified solid cosmetic material, it has been required to achieve high stability in which sweating and the like hardly occur while maintaining a satisfactory feeling of use.

Solution to Problem

According to the present invention, the following invention is provided.
[1] A cosmetic material which is a water-in-oil type emulsified solid cosmetic material including:

an oily component (A);
an aqueous component (B); and
a powder component (C),
in which the oily component contains a polar oil component and a wax component,
the wax component contains an ester wax, a ratio of a total mass of the polar oil component to a total mass of the ester wax is 20 to 70, and
a content of the polar oil component with respect to a total mass of the water-in-oil type emulsified solid cosmetic material is 9 to 30 mass %.
[2] The cosmetic material according to [1], in which a content of water with respect to the total mass of the water-in-oil type emulsified solid cosmetic material is 10 to 25 mass %.
[3] The cosmetic material according to [1] or [2], in which a content of the wax component with respect to the total mass of the water-in-oil type emulsified solid cosmetic material is 3 to 10 mass %.
[4] The cosmetic material according to any one of [1] to [3], in which a content of the ester wax with respect to the total mass of the water-in-oil type emulsified solid cosmetic material is 0.1 to 1.8 mass %.
[5] The cosmetic material according to any one of [1] to [4], in which a content of the ester wax with respect to a total mass of the wax component is 2 to 40 mass %.
[6] The cosmetic material according to any one of [1] to [5], in which the ester wax is a plant-derived wax.
[7] The cosmetic material according to any one of [1] to [6], in which a melting point of the ester wax is 50° C. to 100° C.
[8] The cosmetic material according to any one of [1] to [7], in which the ester wax is carnauba wax.
[9] The cosmetic material according to any one of [1] to [8], in which a rheometer hardness $\gamma$ at 37° C. is 100 or less.

Advantageous Effects of the Invention

According to the present invention, a water-in-oil type emulsified solid cosmetic material having both excellent feeling of use and stability is provided.

BEST MODE FOR CARRYING OUT THE INVENTION

Hereinafter, embodiments of the present invention will be described in detail.

A water-in-oil type emulsified solid cosmetic material (hereinafter, sometimes referred to simply as a cosmetic material) according to the present invention comprises an oily component (A), an aqueous component (B), and a powder component (C) as essential components.

[Oily Component]

The cosmetic material according to the present invention contains a polar oil component and a wax component as the oily component (A).

The polar oil component can be selected and used as necessary from those used in normal cosmetic materials. Specifically, examples thereof include
a liquid ultraviolet absorber (a1) such as octocrylene, 2-ethylhexyl 4-methoxycinnamate, homosalate, 2-ethylhexyl salicylate, hexyl diethylaminohydroxybenzoate, t-butylmethoxydibenzoylmethane, ethylhexyltriazone, and bisethylhexyloxyphenol methoxyphenyltriazine,
an ester oil (a2) such as diisopropyl sebacate, pentaerythrityl tetraethylhexanoate, cetyl ethylhexanoate, jojoba oil, di(phytosteryl/octyldodecyl)lauroyl glutamate, tri-isostearin, glyceryl diisostearate, triethylhexanoin, dimer dilinoleic acid (phytosteryl/behenyl), dimer dilinoleic acid (phytosteryl/isostearyl/cetyl/stearyl/isostearyl/cetyl/stearyl/behenyl), isopropyl palmitate, macadamia nut fatty acid phytosteryl, tetra(behenic acid/benzoic acid/ethylhexanoic acid) pentaerythrityl, ethylhexyl palmitate, myristyl myristate, isopropyl myristate, tripropylene glycol dipivalate, and isodecyl neopentanoate, and the like. In a case where the cosmetic material according to the present invention is used as a sunscreen cosmetic material, it is preferable to use the liquid ultraviolet absorber (a1). The polar oil is not limited thereto, and any polar oil can be combined as necessary within a range in which an effect of the present invention is not impaired.

In the cosmetic material according to the present invention, an oil content of the polar oil component can be adjusted depending on the purpose. However, a content of the polar oil component with respect to the total mass of the cosmetic material needs to be 9 to 30 mass %, and is preferably 10 to 25 mass %. By appropriately adjusting the content of the polar oil, sweating of the cosmetic material can be suppressed.

In addition, in the present invention, the wax component is a non-liquid oily material. The wax component can also be selected and used as necessary from those used in normal cosmetic materials. Specific examples thereof include a carnauba wax, a candelilla wax, a sunflower seed wax, a beeswax, a cotton wax, a bayberry wax, an insect wax, a spermaceti wax, a montan wax, a rice wax, a kapok wax, a Japan wax, a lanolin acetate, a liquid lanolin, a sugar beet wax, lanolin fatty acid isopropyl, hexyl laurate, reduced lanolin, jojoba wax, hard lanolin, a shellac wax, a beeswax, a microcrystalline wax, a paraffin wax, POE lanolin alcohol ether, POE lanolin alcohol acetate, POE cholesterol ether, lanolin fatty acid polyethylene glycol, fatty acid glyceride, hydrogenated castor oil, petroleum jelly, and POE hydrogenated lanolin alcohol ether. In the present invention, the wax component may be a combination of the above-mentioned waxes or other waxes.

In the cosmetic material according to the present invention, the content of the wax component can be discretionally adjusted depending on the purpose, but the content of the wax component with respect to the total mass of the cosmetic material is preferably 3 to 10 mass % and preferably 5 to 8 mass %. By appropriately adjusting the content of the wax component, an appropriate level as a solid cosmetic material can be maintained.

In addition, although various materials for a wax component can be combined in the cosmetic material in the present invention, it is necessary that an ester wax be contained. The ester wax is an ester of a long chain fatty acid and a long chain alcohol, and is generally called a "wax" in some cases. In the present invention, the ester wax is preferably a plant-derived wax. Specifically, a carnauba wax and a candelilla wax are preferably used, and a carnauba wax is particularly preferably used. By using such an ester wax, sweating of the cosmetic material can be suppressed. On the other hand, when the content of the ester wax is excessively high, hardness of the cosmetic material may be insufficient. Therefore, the content of the ester wax is preferably 2 to 40 mass %, and more preferably 2 to 20 mass %, on the basis of a total mass of the wax component.

Furthermore, the content of the ester wax with respect to the total mass of the cosmetic material is preferably 0.1 to 1.8 mass % and more preferably 0.1 to 1.2 mass %. By appropriately adjusting the content of the ester wax, the stability of the cosmetic material tends to be improved, and sweating and the like tend to be suppressed. Since when the content of the ester wax is excessively high, the hardness of the cosmetic material may be insufficient, it is thus necessary to pay attention to this.

In addition, a melting point of the ester wax is preferably 50° C. to 100° C. When the melting point of the ester wax is within this range, spreading is improved when the cosmetic material is applied to the skin, and excellent feeling of use can be obtained.

The cosmetic material according to the present invention may contain various oily materials as necessary, in addition to the polar oil component and the wax component as the oily component. Specifically, examples of a liquid oil or fat include avocado oil, camellia oil, macadamia nut oil, mink oil, olive oil, castor oil, jojoba oil, triglycerin, glycerin trioctanoate, and the like, examples of a solid oil or fat include coconut oil, hydrogenated coconut oil, palm oil, beef tallow, mutton fat, Japan wax, hydrogenated castor oil, and the like, examples of a higher fatty acid include lauric acid, myristic acid, palmitic acid, stearic acid, behenic acid, oleic acid, 12-hydroxystearic acid, isostearic acid, linoleic acid, linoleic acid, and the like, examples of a higher alcohol include lauryl alcohol, cetyl alcohol, stearyl alcohol, behenyl alcohol, oleyl alcohol, monostearyl glycerol ether, monopalmityl glycerol ether, cholesterol, phytosterol, isostearyl alcohol, and the like, examples of an ester oil include isopropyl myristate, cetyl octoate, octyldodecyl myristate, butyl stearate, decyl oleate, ethylene glycol dioctoate, subisostearyl malate, trimethylolpropane trioctanoate, trimethylolpropane triisostearate, pentaerythritol tetraoctoate, glyceryl trioctanoate, glyceryl triisostearate, ethyl acetate, butyl acetate, amyl acetate, and the like, examples of a silicone include dimethylpolysiloxane, methylphenylpolysiloxane, methylhydrogenpolysiloxane, decamethylcyclopentasiloxane, octamethylcyclotetrasiloxane, a silicone resin forming a three-dimensional network structure, silicone rubber, and the like, and examples of a modified silicone include PEG-10 dimethicone, bisbutyl dimethicone polyglyceryl-3, cetyl dimethicone copolyol, lauryl PEG-9 polydimethylsiloxyethyl dimethicone, PEG/PPG-19/19 dimethicone, PEG-9 polydimethylsiloxyethyl dimethicone, (dimethicone/(PEG-10/15)) crosspolymer, polysilicone-13, and the like.

The oily material is not limited thereto, and one kind or two or more kinds can be discretionally selected and used.

In addition, in the cosmetic material according to the present invention, a ratio of the total mass of the polar oil component with respect to a total mass of the ester wax needs to be 20 to 70, and is preferably 25 to 60. When a formulation ratio of the ester wax and the polar oil is within a specific range, the effect of the present invention is significantly exhibited.

[Aqueous Component]

The water-in-oil type emulsified solid cosmetic material according to the present invention contains water and a hydrophilic component that can be usually formulated in a cosmetic material or the like. Examples of the hydrophilic component include, but are not limited to, a humectant, a water-soluble polymer, a water-soluble agent, a sequestering agent, an antioxidant, a thickener, and the like.

Examples of the moisturizing agent include 1,3-butylene glycol, polyethylene glycol, propylene glycol, dipropylene glycol, hexylene glycol, glycerin, diglycerin, xylitol, maltitol, maltose, D-mannitol, and the like.

Examples of the water-soluble polymer include a plant-based polymer such as gum arabic, carrageenan, pectin, agar, quince seed (marmelo), starch, and algae colloid (brown algae extract), a microorganism-based polymer such as dextran and pullulan, an animal-based polymer such as collagen, casein, and gelatin, a starch-based polymer such as carboxymethyl starch and methyl hydroxypropyl starch, an alginic acid-based polymer such as sodium alginate, a vinyl-based polymer such as a carboxyvinyl polymer (CARBOPOL and the like), a polyoxyethylene-based polymer, a polyoxyethylene polyoxypropylene copolymer-based polymer, an acrylic polymer such as sodium polyacrylate and polyacrylamide, and an inorganic water-soluble polymer such as bentonite, magnesium aluminum silicate, and laponite.

Examples of the water-soluble agent include vitamins such as vitamin A, retinol, retinol palmitate, inositol, pyridoxine hydrochloride, benzyl nicotinate, nicotinic acid amide, dl-$\alpha$-tocopherol nicotinate, magnesium ascorbate phosphate, ascorbic acid 2-glucoside, vitamin D2 (ergocalciferol), dl-$\alpha$-tocopherol 2-L ascorbic acid phosphate diester potassium salt, dl-$\alpha$-tocopherol, dl-$\alpha$-tocopherol acetate, pantothenic acid, and biotin, an anti-inflammatory agent such as allantoin and azulene, a whitening agent such as arbutin, an astringent such as zinc oxide and tannic acid, sulfur, lysozyme chloride, pyridoxine hydrochloride, $\gamma$-oryzanol, and the like.

Examples of the sequestering agent include edetate sodium salt, sodium metaphosphate, and phosphoric acid.

Examples of the antioxidant include ascorbic acid, $\alpha$-tocopherol, dibutylhydroxytoluene, and butylhydroxyanisole.

Examples of the thickener include polysaccharides, a synthetic polymer compound, and clay minerals.

In addition, when the cosmetic material according to the present invention contains an appropriate amount of water, it is possible to impart excellent feeling of use and maintain appropriate hardness. Specifically, the content of water with respect to the total mass of the cosmetic material is preferably 10 to 25 mass %.

[Powder Component]

The cosmetic material according to the present invention contains the powder component (C). The powder that can be formulated in the cosmetic material according to the present invention can be discretionally selected and used from powders used in normal in the cosmetic material. Specifically, examples thereof include an inorganic powder such as talc, kaolin, mica, sericite (sericite), muscovite, biotite, phlogopite, synthetic mica, vermiculite, magnesium carbonate, calcium carbonate, aluminum silicate, barium silicate, calcium silicate, magnesium silicate, metal tungstate, magnesium, silica, zeolite, barium sulfate, calcined calcium sulfate, calcined gypsum, calcium phosphate, fluorapatite, hydroxyapatite, ceramic powders, and metal soaps (for example, zinc myristate, calcium palmitate, aluminum stearate, and the like), an organic powder such as a polyamide resin powder, a polyethylene powder, a polymethyl methacrylate powder, a polystyrene powder, a styrene-acrylic acid copolymer resin powder, a benzoguanamine resin powder, a polytetrafluoroethylene powder, and a cellulose powder, an inorganic white-based pigment such as titanium oxide and zinc oxide, inorganic red-based pigments such as iron oxide (Bengala) and iron titanate, an inorganic brown-based pigment such as $\gamma$-iron oxide, an inorganic yellow-based pigment such as yellow iron oxide and yellow earth, an inorganic black-based pigment such as black iron oxide, carbon, and lower titanium oxide, an inorganic violet-based pigment such as mango violet and cobalt violet, an inorganic green-based pigment such as chromium oxide hydroxide and cobalt titanate, an inorganic blue-based pigment such as ultramarine blue and Prussian blue, a pearl pigment such as titanium oxide-coated mica, titanium oxide-coated bismuth oxychloride, titanium oxide-coated talc, colored titanium oxide-coated mica, bismuth oxychloride, and fish scale foil, a metallic powder pigment such as an aluminum powder and a kappa powder, and a lake pigment such as a zirconium lake, a barium lake, and an aluminum lake of an organic pigment such as Red No. 202, Red No. 205, Red No. 220, Red No. 228, Red No. 405, Orange No. 203, Orange No. 204, Yellow No. 205, Yellow No. 401, and Blue No. 404 and an organic pigment such as Red No. 3, Red No. 104, Red No. 227, Red No. 401, Orange No. 205, Yellow No. 4, Yellow No. 202, Green No. 3, and Blue No. 1, and natural color such as chlorophyll and $\beta$-carotene. Among these, titanium oxide, iron oxide, silica, and the like are preferably used, and those subjected to a hydrophobic treatment are particularly preferable.

[Cosmetic Material]

The cosmetic material according to the present invention contains the above-described components, and the cosmetic material is molded into a product. The form of the cosmetic material according to the present invention is not particularly limited, and for example, forms such as a makeup base, foundation, white powder, blusher, lipstick, mascara, eye shadow, and eye liner can be adopted. In particular, it is preferable that the molded cosmetic material is accommodated in a compact container. The water-in-oil type emulsified solid cosmetic material according to the present invention has appropriate hardness, and thus is easy to take on a puff or the like, and is easy to spread uniformly when applied to the skin. More specifically, the cosmetic material according to the present invention preferably has a rheometer hardness $\gamma$ of 100 or less at 37° C. Note that, in the present invention, regarding the rheometer hardness $\gamma$, a value calculated according to the following equation, from a measured value obtained by using a rheometer (manufactured by Fudo Kogyo Co., Ltd.) under conditions of, load: 2 kg needle diameter: 3 mmφ penetration speed: 2 cm/min penetration distance: 1 mm measurement temperature: 37° C.

was defined as a hardness γ.

$\gamma = (G*L)/(I*a)$ (dyn/cm$^2$)

(in the equation:

G: measured stress (gr)×980 dyn

L: thickness of sample (mm)

I: compression distance (mm)

a: cross-sectional area of needle (cm$^2$))

EXAMPLES

Examples 1 and 2 and Comparative Example 1

Cosmetic materials of each of Examples and Comparative Examples were prepared with the formulations shown in Table 1.

Furthermore, regarding the performance of these cosmetic materials, the stability and usability of the cosmetic materials were evaluated according to the following criteria.

B: There is almost no change in the surface of the cosmetic material.

C: Droplets or irregularities are generated on the surface of the cosmetic material.

Usability of Cosmetic Material

The cosmetic material was rubbed with a puff, and the feeling of use when applied to the face of each panel was evaluated according to the following criteria.

A: Spreading on the skin is good and the cosmetic material spreads evenly

B: Spreading on the skin is slightly poor, but there is no problem in use

C: Spreading on the skin is insufficient

D: The cosmetic material comes off in clumps when rubbed off with a puff, and thus it is difficult to apply evenly.

TABLE 1

| | | component | Comparative Example 1 | Example 1 | Example 2 |
|---|---|---|---|---|---|
| oily component | polar oil | octocrylene | 3 | 5 | 5 |
| | | ethylhexyl methoxysilate | — | — | 5 |
| | | homosalate | 10 | 10 | |
| | | ethylhexyl salicylate | 5 | 5 | |
| | wax | mixture of paraffin wax wax and microcrystalline wax | 7.5 | 5.4 | 5.4 |
| | | mixture of polyethylene wax wax and microcrystalline wax | 1.5 | 1.8 | 1.8 |
| | ester wax | carnauba wax | | 0.36 | 0.36 |
| | | dimethicone (2 cs) | residue | residue | residue |
| | | PEG-10 dimethicone | 2 | 2 | 2 |
| | | bisbutyl dimethicone polyglyceryl-3 | 2 | 2 | 2 |
| | | distearyldimonium chloride | 0.2 | 0.2 | 0.2 |
| | | palmitic acid | 0.15 | 0.15 | 0.15 |
| | | disteardimonium hectorite | 0.1 | 0.1 | 0.1 |
| powder component | | silicone-treated fine titanium dioxide *[1] | 12 | 12 | 12 |
| | | silicone-treated fine titanium dioxide *[2] | 4 | 4 | 4 |
| | | silicone-treated iron oxide (red) | 0.63 | 0.63 | 0.63 |
| | | silicone-treated iron oxide (yellow) | 1.5 | 1.5 | 1.5 |
| | | silicone-treated iron oxide (black) | 0.04 | 0.04 | 0.04 |
| | | silicone-treated pigment grade titanium dioxide | 8.5 | 8.5 | 8.5 |
| | | silica | 1 | 1 | 1 |
| aqueous component | water | deionized water | 12 | 12 | 12 |
| | | dipropylene glycol | 6 | 6 | 6 |
| | | glycerin | 1 | 1 | 1 |
| | | preservative (paraben) antioxidant, etc | q.s. | q.s. | q.s. |
| | | total | 100 | 100 | 100 |
| | | content of the polar oil (mass %) | 18 | 20 | 10 |
| | | content of the wax (mass %) | 9 | 7.56 | 7.56 |
| | | content of the ester wax with respect to total mass of the wax component (mass %) | 0 | 4.76 | 4.76 |
| | | ratio of [(total mass of the polar oil)/(a total mass of the ester wax)] | N/A | 55.6 | 55.6 |
| | evaluation | sweating stability | C | A | A |
| | | usability | C | B | A |

*[1] STR-100C-LP (trade neme, Sakai Chemical Industry Co., Ltd)

*[2] MT-500SAS (trade name, Tayca Co., Ltd)

Evaluation Method

Sweating Stability of Cosmetic Material

A sample stored at 50° C. for 2 weeks was taken out under the condition of 25° C., and it was confirmed whether sweating (oil droplets) could be visually observed on a sufficiently cooled sample surface.

A: Sweating or the like is not observed at all on the surface of the cosmetic material, which is good.

Examples 3 to 5 and Comparative Examples 2 to 5

Cosmetic materials of each of Examples and Comparative Examples were prepared with the formulations shown in Table 1.

Furthermore, regarding the performance of these cosmetic materials, the stability, usability, and rheometer hardness of the cosmetic materials were evaluated.

TABLE 2

| | | component | Example 3 | Comparative Example 2 | Comparative Example 3 | Comparative Example 4 | Example 4 | Comparative Example 5 | Example 5 |
|---|---|---|---|---|---|---|---|---|---|
| oily component | polar oil | octocrylene | 5 | 5 | 5 | 5 | 5 | 5 | 5 |
| | | ethylhexyl methoxysilate | 5 | 5 | 5 | 5 | 5 | 5 | 5 |
| | wax | mixture of paraffin wax wax and microcrystalline wax | 5.4 | 8.6 | 5.4 | 3.76 | 5.4 | | 5.4 |
| | | mixture of polyethylene wax wax and microcrystalline wax | 1.8 | 2.9 | 1.8 | 1.26 | 1.8 | | 1.8 |
| | ester wax | carnauba wax | 0.36 | 0.6 | 0.1 | 4 | | | 0.36 |
| | | candelilla wax | | | | | | 7.56 | |
| | | sunflower seed wax | | | | | 0.36 | | |
| | | dimethicone (2cs) | residue | residue | residue | residue | residue | residue | residue |
| | | PEG-10 dimethicone | 2 | 2 | 2 | 2 | 2 | 2 | 2 |
| | | bisbutyl dimethicone polyglyceryl-3 | 2 | 2 | 2 | 2 | 2 | 2 | 2 |
| | | distearyldimonium chloride | 0.2 | 0.2 | 0.2 | 0.2 | 0.2 | 0.2 | 0.2 |
| | | palmitic acid | 0.15 | 0.15 | 0.15 | 0.15 | 0.15 | 0.15 | 0.15 |
| | | disteardimonium hectorite | 0.1 | 0.1 | 0.1 | 0.1 | 0.1 | 0.1 | 0.1 |
| powder component | | silicone-treated fine titanium dioxide *1 | 12 | 12 | 12 | 12 | 12 | 12 | 12 |
| | | silicone-treated fine titanium dioxide *2 | 4 | 4 | 4 | 4 | 4 | 4 | 4 |
| | | silicone-treated iron oxide (red) | 0.63 | 0.63 | 0.63 | 0.63 | 0.63 | 0.63 | 0.63 |
| | | silicone-treated iron oxide (yellow) | 1.5 | 1.5 | 1.5 | 1.5 | 1.5 | 1.5 | 1.5 |
| | | silicone-treated iron oxide (black) | 0.04 | 0.04 | 0.04 | 0.04 | 0.04 | 0.04 | 0.04 |
| | | silicone-treated pigment grade titanium dioxide | 8.5 | 8.5 | 8.5 | 8.5 | 8.5 | 8.5 | 8.5 |
| | | silica | 1 | 1 | 1 | 1 | 1 | 1 | 1 |
| aqueous component | water | deionized water | 17 | 12 | 17 | 15 | 17 | 17 | 5 |
| | | dipropylene glycol | 6 | 6 | 6 | 6 | 6 | 6 | 6 |
| | | glycerin | 1 | 1 | 1 | 1 | 1 | 1 | 1 |
| | | preservative (paraben) antioxidant, etc | q.s. | q.s. | q.s. | q.s. | q.s. | q.s. | q.s. |
| total | | | 100 | 100 | 100 | 100 | 100 | 100 | 100 |
| content of the polar oil (mass %) | | | 10 | 10 | 10 | 10 | 10 | 10 | 10 |
| content of the wax (mass %) | | | 7.56 | 12.1 | 7.3 | 9.02 | 7.56 | 7.56 | 7.56 |
| content of the ester wax with respect to total mass of the wax component (mass %) | | | 4.76 | 4.96 | 1.37 | 44.34 | 4.76 | 100 | 4.76 |
| ratio of [(total mass of the polar oil)/ (a total mass of the ester wax)] | | | 27.8 | 16.7 | 1000 | 2.5 | 27.8 | 1.32 | 27.8 |
| evaluation | | sweating stability | A | A | C | C | A | C | A |
| | | usability | A | D | B | D | A | D | C |
| | | rheometer hardness (37° C.) | 71 | 134 | 57 | 113 | 61 | 60 | 82 |

*1 STR-100C-LP (trade neme, Sakai Chemical Industry Co., Ltd)
*2 MT-500SAS (trade name, Tayca Co., Ltd)

From the above results, it is found that when the oily component in the water-in-oil type emulsified solid cosmetic material contains a polar oil and an ester wax, and contents thereof are in a specific range, excellent stability and usability can be achieved.

The invention claimed is:

1. A cosmetic material which is a water-in-oil type emulsified solid cosmetic material comprising:
an oily component (A);
an aqueous component (B); and
a powder component (C),
wherein the oily component contains a polar oil component and a wax component,
the wax component contains an ester wax, a ratio of a total mass of the polar oil component to a total mass of the ester wax is 20 to 70,
a content of the polar oil component with respect to a total mass of the water-in-oil type emulsified solid cosmetic material is 9 to 30 mass %, and a content of water with respect to the total mass of the water-in-oil type emulsified solid cosmetic material is 10 to 25 mass %.

2. The cosmetic material according to claim 1, wherein a content of the wax component with respect to the total mass of the water-in-oil type emulsified solid cosmetic material is 3 to 10 mass %.

3. The cosmetic material according to claim 1, wherein a content of the ester wax with respect to the total mass of the water-in-oil type emulsified solid cosmetic material is 0.1 to 1.8 mass %.

4. The cosmetic material according to claim 1, wherein a content of the ester wax with respect to a total mass of the wax component is 2 to 40 mass %.

5. The cosmetic material according to claim 1, wherein the ester wax is a plant-derived wax.

6. The cosmetic material according to claim 1, wherein a melting point of the ester wax is 50° C. to 100° C.

7. The cosmetic material according to claim 1, wherein the ester wax is carnauba wax.

8. The cosmetic material according to claim 1, wherein a rheometer hardness $\gamma$ at 37° C. is 100 or less.

\* \* \* \* \*